United States Patent
Renzi et al.

(10) Patent No.: US 9,579,649 B2
(45) Date of Patent: Feb. 28, 2017

(54) FLUID DELIVERY MANIFOLDS AND MICROFLUIDIC SYSTEMS

(75) Inventors: Ronald F. Renzi, Tracy, CA (US); Gregory J. Sommer, Livermore, CA (US); Anup K. Singh, Danville, CA (US); Anson V. Hatch, Tracy, CA (US); Mark R. Claudnic, Livermore, CA (US); Ying-Chih Wang, Pleasanton, CA (US); James L. Van de Vreugde, Livermore, CA (US)

(73) Assignee: Sandia Corporation, Albuquerque, NM (US)

( * ) Notice: Subject to any disclaimer, the term of this patent is extended or adjusted under 35 U.S.C. 154(b) by 1051 days.

(21) Appl. No.: 12/900,276

(22) Filed: Oct. 7, 2010

(65) Prior Publication Data

US 2012/0085644 A1   Apr. 12, 2012

(51) Int. Cl.
  *G01N 35/00* (2006.01)
  *G01N 35/10* (2006.01)
  *B01L 3/00* (2006.01)

(52) U.S. Cl.
  CPC ......... *B01L 3/502715* (2013.01); *B01L 3/56* (2013.01); *B01L 2200/027* (2013.01); *B01L 2300/0816* (2013.01); *B01L 2400/0421* (2013.01); *B01L 2400/0487* (2013.01); *G01N 35/1095* (2013.01); *G01N 2035/00158* (2013.01); *Y10T 137/6851* (2015.04)

(58) Field of Classification Search
  CPC .......... B01L 3/502715; B01L 3/56; B01L 2200/027; B01L 2200/0816; B01L 2200/0421; B01L 2200/0487; Y10T 137/6851; G01N 35/1095; G01N 2035/00158
  USPC .................................................. 422/500–507
  See application file for complete search history.

(56) References Cited

U.S. PATENT DOCUMENTS 5,726,026 A * 3/1998 Wilding et al. ............. 435/7.21
6,123,820 A * 9/2000 Bergkuist et al. ............ 204/411

* cited by examiner

*Primary Examiner* — Lyle Alexander
*Assistant Examiner* — Robert Eom
(74) *Attorney, Agent, or Firm* — Dorsey & Whitney, LLP

(57) ABSTRACT

Embodiments of fluid distribution manifolds, cartridges, and microfluidic systems are described herein. Fluid distribution manifolds may include an insert member and a manifold base and may define a substantially closed channel within the manifold when the insert member is press-fit into the base. Cartridges described herein may allow for simultaneous electrical and fluidic interconnection with an electrical multiplex board and may be held in place using magnetic attraction.

15 Claims, 9 Drawing Sheets

US 9,579,649 B2

FLUID DELIVERY MANIFOLDS AND MICROFLUIDIC SYSTEMS

STATEMENT REGARDING RESEARCH & DEVELOPMENT

The United States Government has a paid-up license in this invention and the right in limited circumstances to require the patent owner to license others on reasonable terms as provided for by the terms of contract No. DE-AC04-94AL85000 awarded by the U.S. Department of Energy to Sandia Corporation.

BACKGROUND

Microfluidic systems and applications continue to increase in complexity. As microfluidic analysis techniques in the laboratory continue to promise lower-cost, higher-efficiency biological and chemical fluid analysis, it is increasingly challenging to produce systems that implement these techniques in a user-friendly manner. For example, it may be challenging to effectively connect fluidic and electronic sources to a microfluidic chip.

Moreover, multiplexing designs are increasingly being integrated into a single chip. A multiplexing assay may advantageously route many fluidic channels through a microfluidic process and/or detection region on chip. It may be challenging to route fluids to the larger number of on-chip locations required for multiplexing applications. For example, if a fairly large pipette or other plumbing interface is used to make an external fluidic connection to a chip, that interface may consume a relatively large area. Making many of those connections to multiple locations on a chip may be cumbersome or unduly constrict an overall device size.

Still further, it has been challenging to integrate electrical control to microfluidic systems. For example, in some microfluidic systems, fluid motion may be controlled using the application of one or more voltages to the fluids—e.g. to effect electrophoretic flow. Microfluidic systems may utilize conductive pins placed into an open, fluid-filled reservoir to apply a potential to a fluid reservoir and/or create a potential difference between two reservoirs. Such an interconnection relies on open fluid-filled reservoirs in which to place the conductive pins.

Still further, many microfluidic systems may require well-trained personnel to operate the systems. Many systems require manual application of electronic and/or fluidic control signals to perform fluidic analysis. Many systems also may be cumbersome to use for multiple samples, requiring extensive washing to ensure no sample contamination between analysis. Systems may also be difficult to use for different analysis techniques, being generally configured for a single analysis or detection modality and requiring a skilled operator to perform the analysis manually.

DETAILED DESCRIPTION

Certain details are set forth below to provide a sufficient understanding of embodiments of the invention. However, it will be clear to one skilled in the art that embodiments of the invention may be practiced without various of these particular details. In some instances, well-known circuits, control signals, timing protocols, software operations, materials, particles, reagents, fluids, samples, labels, and analytes may not have been shown in detail in order to avoid unnecessarily obscuring the described embodiments of the invention.

Embodiments of the present invention include fluid distribution manifolds that may be used to route fluids from one inlet location to multiple outlet locations in fluid communication with a microfluidic chip. The fluid distribution manifolds will be described further below and may advantageously reduce a number of fluid interconnects that may be needed directly to a microfluidic chip from an external fluid source.

Figure 1:
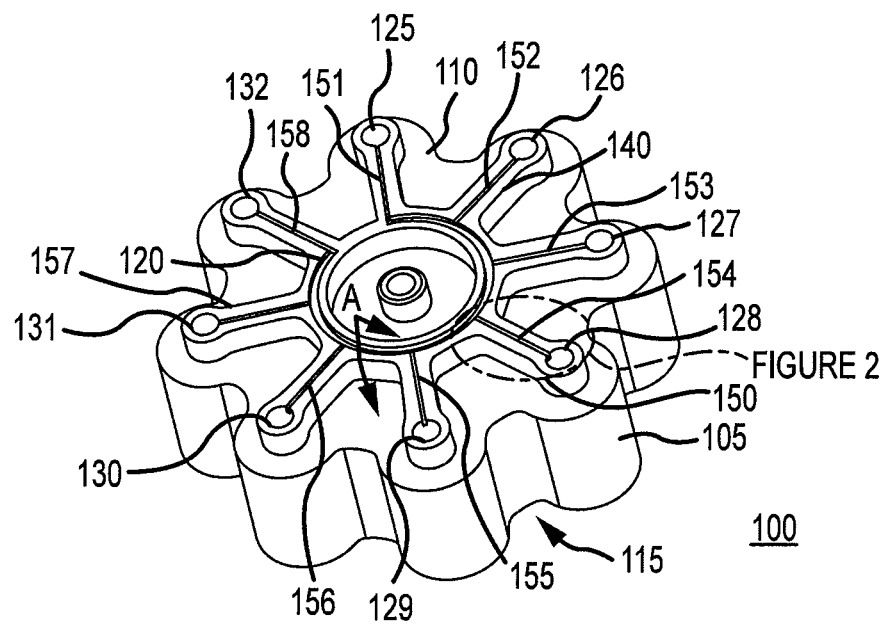
FIG. 1 is a schematic illustration of an insert member 100 arranged in accordance with an embodiment of the present invention.

FIG. 1 is a schematic illustration of an insert member 100 arranged in accordance with an embodiment of the present invention. The insert member 100 has a shape (shown with curved outer periphery 105 in FIG. 1), a first surface 110, a second surface 115, and defines at least one channel 120 in the first surface 110. The channel 120 is configured for fluid communication between an inlet location 125 and multiple outlet locations 126-132. In the example of FIG. 1, the channel 120 connects to multiple secondary channels 151-158, each configured for fluid communication with a respective inlet or outlet location.

The insert member 100 may generally be formed of any machinable material, including but not limited to polymeric materials. The channel 120 may be machined, embossed, or otherwise created in the surface 110 of the insert member 100. Any number of inlet and outlet locations may generally be provided. The surface 110 of the insert member 100 includes a raised portion 140 on the surface 110 into which the channel 120 is defined, however, the raised portion 140 may not be implemented in all embodiments, and the channel 120 may be defined recessed directly from the surface 110. One or more of the inlet location 125 and the outlet locations 126-132 may be implemented as through-holes from the surface 110 to the opposite surface 115 of the insert member 100 depending on the desired orientation of a microfluidic chip (in fluid communication with the outlet locations 126-132) and fluid source (in fluid communication with the inlet location 125).

Other configurations are possible. For example, the locations 125-132 may all be in fluid communication with a microfluidic chip. An inlet location may be implemented as a through-hole emerging at a location near a 'start' of the channel 120, such as near the junction of the channel 151 and the channel 120. An outlet location may be implemented as another through-hole emerging at a location near an 'end' of the channel 120, such as near the junction of the channel 158 and the channel 120. If you look closely the inner diameter fluid channel has a definitive starting point and ending point. There may be corresponding ports on the opposite side of the insert member so that fluid may be introduced to the channel 120 and distributed to the locations 125-132 and may be flowed out from and end of the channel 120. This may be used for example to remove excess fluid, overflow, suction point, or for sample flushing.

Figure 2:
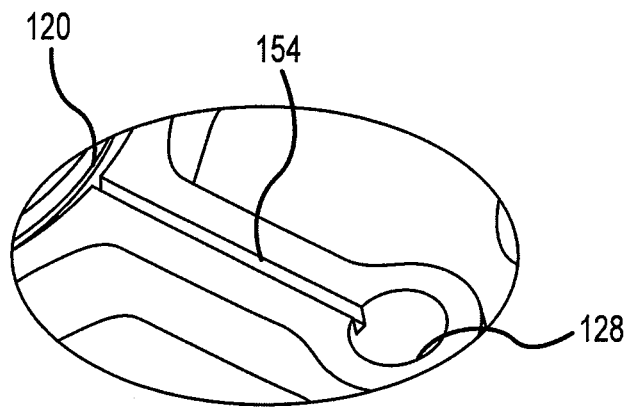
FIG. 2 is a schematic illustration of a region 150 of the insert member 100.

FIG. 2 is a schematic illustration of a region 150 of the insert member 100. The region includes a portion of the channel 120 and a secondary channel 154 leading to outlet location 128. The channel 120 connecting to the secondary channel 154 may have a larger cross-sectional size in some embodiments than the secondary channel 154. This may advantageously allow the flow from the channel 120 to the smaller channel 154 to be controlled through the pressure of the applied fluid in some embodiments. However, on other embodiments, the cross-sectional areas of the channel 120 and the secondary channel 154 may be substantially similar such that fluid flow occurs through both with a same applied pressure. Generally, any dimensions may be used for the channel 120, inlet location 125, and outlet locations 126-132. In some embodiments, the channel 120 and secondary channels 151-158 have widths less than or equal to 1 mm, in some embodiments less than or equal to 500 microns, in some embodiments, less than or equal to 200 microns, in some embodiments, less than or equal to 150 microns. Other dimensions, including smaller dimensions, may be used. In one embodiment, the channel 120 may have a width of 400 microns while the channel 154 has a width of 125 microns. Similarly, the inlet location 125 and outlet locations 126-132 may have substantially any size, in one embodiment, the inlet location 125 and outlet locations 126-132 may include a 1.5 mm via, such as the via 128 shown in FIG. 2. As stated above, in some embodiments the inlet location 125 and/or outlet locations 126-132 may include a through-hole through the insert member 100 from the surface 110 to the opposite surface 115.

Figure 3:
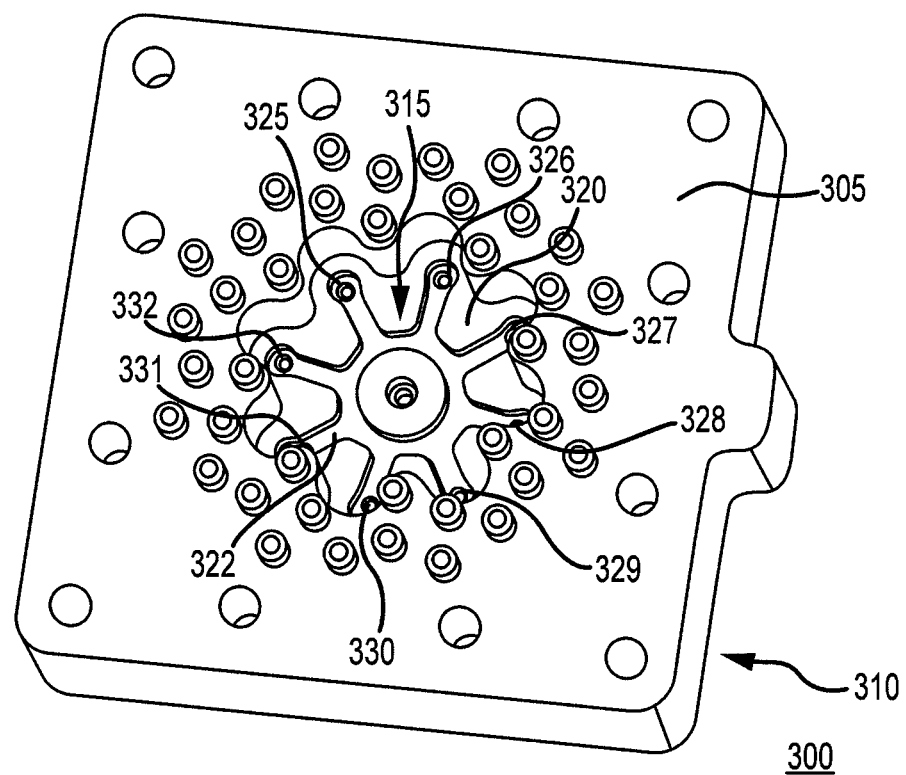
FIG. 3 is a schematic illustration of a manifold base 300 arranged in accordance with an embodiment of the present invention and configured for use with the insert member 100.

The insert member 100 is designed for insertion into a manifold base. FIG. 3 is a schematic illustration of a manifold base 300 arranged in accordance with an embodiment of the present invention and configured for use with the insert member 100. The manifold base 300 includes a first surface 305 and a second surface 310. The manifold base 300 at least partially defines an indentation 315 having a shape configured to receive the insert member 100. That is, the shape of the indentation 315 generally corresponds to the shape 105 of the insert member 100, which may facilitate press-fitting the two together, as will be described further below. The indentation 315 results in a recessed surface 320 of the manifold base 300. The recessed surface 320 may include further indentations 322 corresponding to the raised portion 140 of the insert member 100 if present. The manifold base 300 may further include an inlet location 325 and outlet locations 326-332 corresponding to the inlet location 125 and outlet locations 126-132, respectively of the insert member 100. One or more of the inlet location 125 and outlet locations 126-132 may be implemented using through-holes from the recessed surface 315 to the opposite surface 310 of the manifold base 300 depending on a design configuration of the microfluidic chip and fluid sources.

Figure 4:
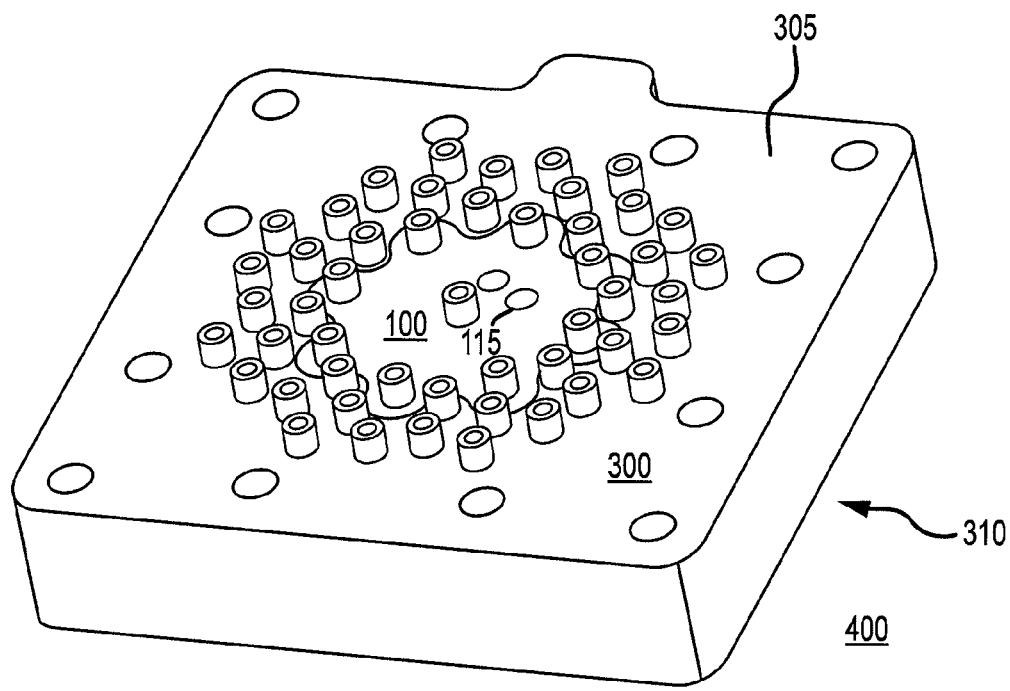
FIG. 4 is a schematic illustration of a fluid distribution manifold 400 arranged in accordance with an embodiment of the present invention.

In this manner, the insert member 100 may be press-fit into the manifold base 300. Once press-fit, the channel 120 in the insert member 100 and the recessed surface 315 of the manifold base 300 may define a substantially closed channel. FIG. 4 is a schematic illustration of a fluid distribution manifold 400 arranged in accordance with an embodiment of the present invention. The insert member 100 has been press-fit into the manifold base 300. By press-fit, herein is meant that the insert member 100 is pressed into the manifold base to form a substantially closed channel. The substantially closed channel may form a fluid-tight seal in that fluid may not leak significantly out of the junction between the manifold base and the insert member. In some embodiments, the shape of the insert member 100 is slightly larger than the shape of the indentation defined by the manifold base 300 to facilitate press-fitting to form a fluid-tight seal. By press-fitting machined parts, bonding, adhesive, or other joining processes may be advantageously avoided or reduced in some embodiments. The press-fitting may be performed manually or by machine. In this manner, a substantially closed channel is formed between the insert member 100 and the manifold base 300.

The manifold base or the insert member or both may additionally have any number of protrusions, shown in FIG. 4. The protrusions may extend above a top surface of the manifold base at the location of one or more through-holes through the manifold base. That is, each protrusion shown in FIG. 4 may correspond to a through-hole through the fluid manifold base or the insert member. The protrusions on the insert member 100 may be in fluid communication with the substantially closed channel, such as in fluid communication with one or more inlet or outlet locations. The protrusions on the fluid distribution manifold 400 may be configured to align with inlet ports of a microfluidic chip, as will be described further below. The protrusions on the fluid distribution manifold 400 may be configured to form a press-fit fluid tight seal with one or more through-holes in an electrical interconnect board, as will also be described further below.

Figure 5:
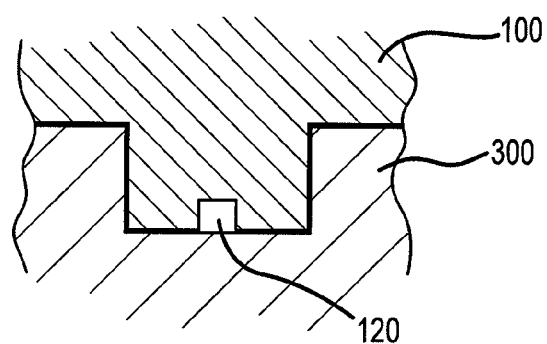
FIG. 5 is a schematic illustration of a cross-section of the fluid manifold 400 along a line of the insert member labeled 'A' in FIG. 1.

For example, FIG. 5 is a schematic illustration of a cross-section of the fluid manifold 400 along a line of the insert member labeled 'A' in FIG. 1. The insert member 100 is press-fit into the fluid manifold base and the channel 120 defined by the insert member 100 is closed by a surface of the manifold base 300.

Accordingly, fluid distribution manifolds have been described above such that fluid may be routed from an inlet location to multiple outlet locations within a fluid manifold via a closed channel within the manifold. The manifold generally includes an insert member press-fit into a manifold base. Through the configuration of through-holes in the insert member, base, or both, a variety of configurations may be achieved. In some examples, the insert member 100 may have a through-hole from the surface 115 through to the inlet location such that fluid from an external source may be routed through the insert member 100 into the closed channel. In some examples, the manifold base 300 may have a through-hole from the surface 310 through to the inlet location such that fluid from an external source may be routed through the manifold base 300 into the closed channel. In some examples, one or more through-holes may be provided from the surface 115 through to respective outlet locations such that a microfluidic chip may be in fluid communication with the through-holes on the surface 115 to receive fluid from the substantially closed channel within the manifold. In some examples, one or more through-holes may be provided from the surface 310 of the manifold base 300 to respective outlet locations such that a microfluidic chip may be in fluid communication with the through-holes on the surface 310 to receive fluid from the substantially closed channel within the manifold. In this manner, embodiments of manifolds may be designed such that any combination of fluid entry and exit locations may be possible. In some embodiments, fluid may enter the manifold 400 from an external source through the surface 115, be routed through the internal channel 120, and also exit from through-holes in the surface 115. In some embodiments, fluid may enter the manifold 400 from an external source through the surface 115, be routed through the internal channel 120, and exit from through-holes to the surface 310. In some embodiments, fluid may enter the manifold 400 from an external source through the surface 310, be routed through the internal channel 120, and also exit from through-holes in the surface 310. In some embodiments, fluid may enter the manifold 400 from an external source through the surface 310, be routed through the internal channel, and exit through through-holes in the surface 115 for fluidic communication to a microfluidic chip.

By fluidic communication herein is meant that a fluid path may exist or be created between two locations. That is, a contiguous channel may be provided between those two locations in some embodiments. In some embodiments, valves or pumps or other fluidic components may be used to control or propel flow along the path. Generally, fluidic communication refers to the ability for a fluid to get from one location or component to the other.

Accordingly, examples of fluid distribution manifolds have been described above that may route fluid through a closed channel defined within the manifold by a press-fit combination of an insert member and a manifold base. These manifolds may allow for one-to-many fluid interconnections to a microfluidic chip. Multiple layers of manifolds may be used in some embodiments to obtain even further fluidic routing.

Embodiments of cartridges for use with, or in some examples containing, a microfluidic chip, will now be described further below. The cartridges may include one or more fluid distribution manifolds as described above. Some examples of cartridges may additionally or instead include reservoirs at least partially defined by a conductive through-hole for application of a voltage to the reservoir.

Figure 6:
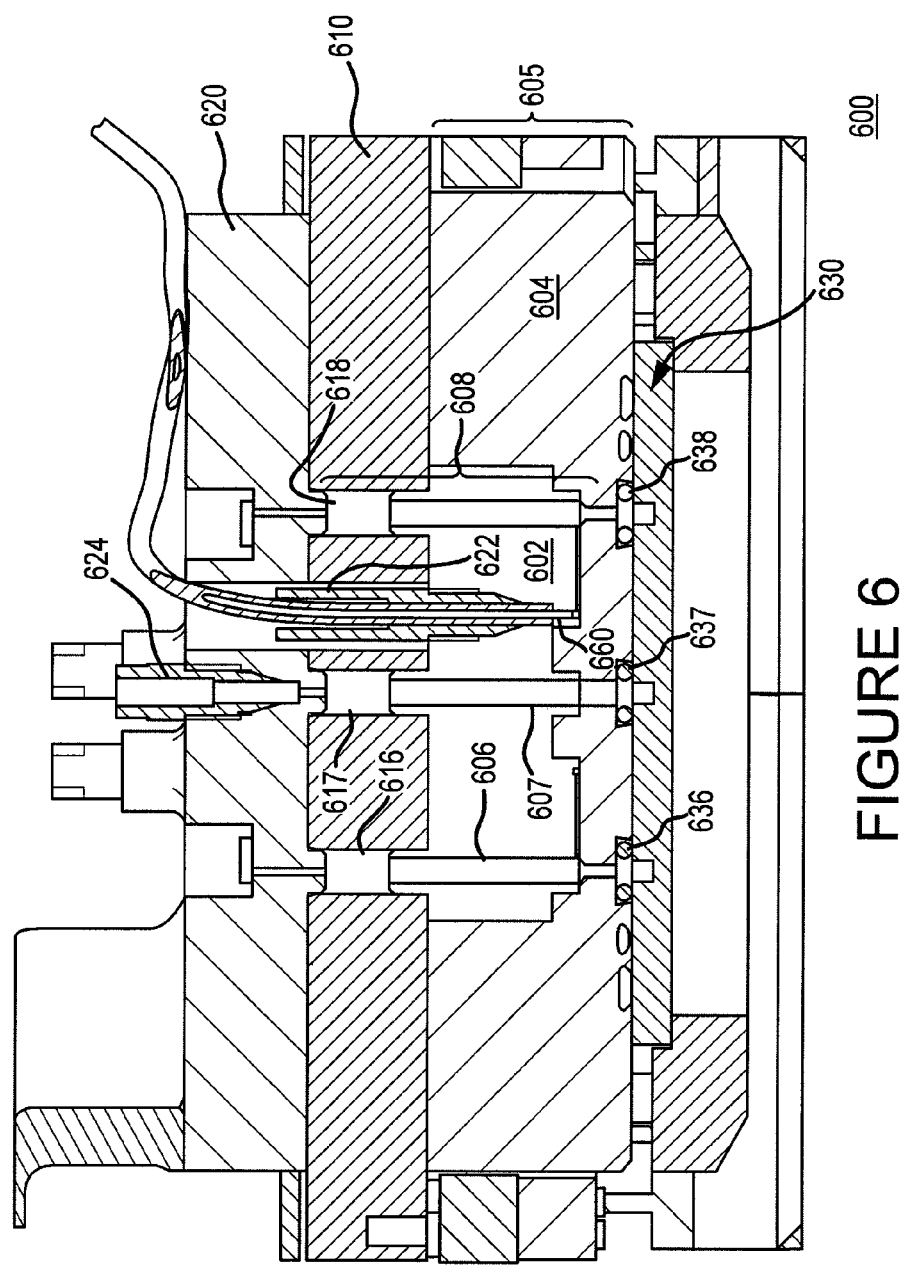
FIG. 6 is a schematic illustration of a cross-section of a cartridge 600 arranged in accordance with an embodiment of the present invention.

FIG. 6 is a schematic illustration of a cross-section of a cartridge 600 arranged in accordance with an embodiment of the present invention. The cartridge may include a fluid distribution manifold 605, which may at least partially define one or more fluid reservoirs, including reservoirs 606, 607, and 608. The cartridge may also include an electrical interconnect board 610. The electrical interconnect board 610 may at least partially define through-holes 616, 617, and 618. The through-holes 616, 617, and 618 may have conductive sidewalls. The conductive sidewalls may allow for the application of a voltage or current to the fluid in the respective reservoir. Although not explicitly shown in the view of FIG. 6, the conductive sidewalls may be coupled to electric traces which may run to electrodes at other locations on the electrical interconnect board 610, as will be described further below. Another fluid distribution manifold may be provided for additional fluid routing in some embodiments. Appropriately sized indentations may be provided to accommodate plumbing ferrules 622 and 624 in some examples for the introduction of fluid into the fluid manifold(s) 620 and 605. O-rings 636, 637, and 638 may be provided at a surface of the fluid distribution manifold 605 to seal an interface between the manifold 605 and a microfluidic chip 630.

The fluid distribution manifolds 620 and 605 may generally be implemented in accordance with the press-fit techniques described above. The fluid distribution manifold 605, for example, may include an insert member 602 and a manifold base 604. An inlet location may be found at location 660, for example, and fluid may be brought into an internal channel by the plumbing ferrule 622. An outlet location may correspond to the reservoir 608, and may be in fluidic communication with the microfluidic chip 630 via an O-ring seal 638.

Substantially any microfluidic chip may be used to implement the microfluidic chip 630. The microfluidic chip 630 generally includes a substrate defining at least one microfluidic channel having a dimension of around 1 mm or less. In some embodiments, 500 μm or less. In some embodiments, the chips include channels having a dimension of around 100 μm or less. Other dimensions may be used. The microfluidic chip 630 may generally also include any number of fluidic chambers that may be used for any of a variety of purposes including one or more incubation, separation, or sample preparation chambers. In some examples, these functions may be performed in the reservoirs 606-608 in addition to or instead of on chip. The microfluidic chip 630 may also include any number of inlet/outlet ports, such as ports corresponding to the O-ring 636, 637, and 638 locations. The microfluidic chip 630 may also include one or more detection channels or chambers configured to detect a signal from a sample introduced into the microfluidic chip. The signal detected may be chemical, electrical, or optical, in accordance with known detection methodologies. The microfluidic chip 630 may generally be implemented using a substrate. The substrate may include any of a variety of materials. In some embodiments, as will be further described below, the substrate may be a quartz substrate. Quartz, glass, polycarbonate, fused-silica, PDMS, and other transparent substrates may be desired in some embodiments to allow optical observation of sample within the channels and chambers of the chip 630. In some embodiments, however, a plastic, metal or semiconductor substrate may be used. Microscale fabrication techniques, generally known in the art, may be utilized to fabricate the microfluidic chip 630. The microscale fabrication techniques employed to fabricate the chip 630 may include, for example, etching, surface treatments, photolithography, bonding and other techniques.

Embodiments of the electrical interconnect board 610 will be described further below. The electrical interconnect board 610 may define one or more through-holes, such as the through-holes 616-618 of FIG. 6. The through-holes are in fluidic communication with the reservoirs 606-608 in the fluid distribution manifold 605. The through-holes have conductive sidewalls, and may accordingly make electronic connection to fluid in the respective reservoirs 606-608. The conductive sidewalls may be achieved in generally any manner, including plating a conductive material onto the sidewalls of through-holes in a substrate used to implement the electrical interconnect board 610. The substrate may include, for example, a printed circuit board, although other substrates may be used. In some examples, the conductive sidewalls may themselves be in contact with fluid in the reservoirs, and in some examples, an insulating or other protective layer may be between the conductive sidewalls and the fluid. A voltage may be applied to the fluid in the reservoirs by applying a voltage to the conductive sidewalls, for example, by applying a voltage to an electrode in electronic communication with the conductive sidewall. In this manner, the reservoirs 606-608 may be closed, for example, by the fluid manifold 620, and a voltage applied to the closed reservoir. This may be in contrast to systems where a voltage is applied to a reservoir through use of a pin inserted into the open reservoir.

Figure 7:
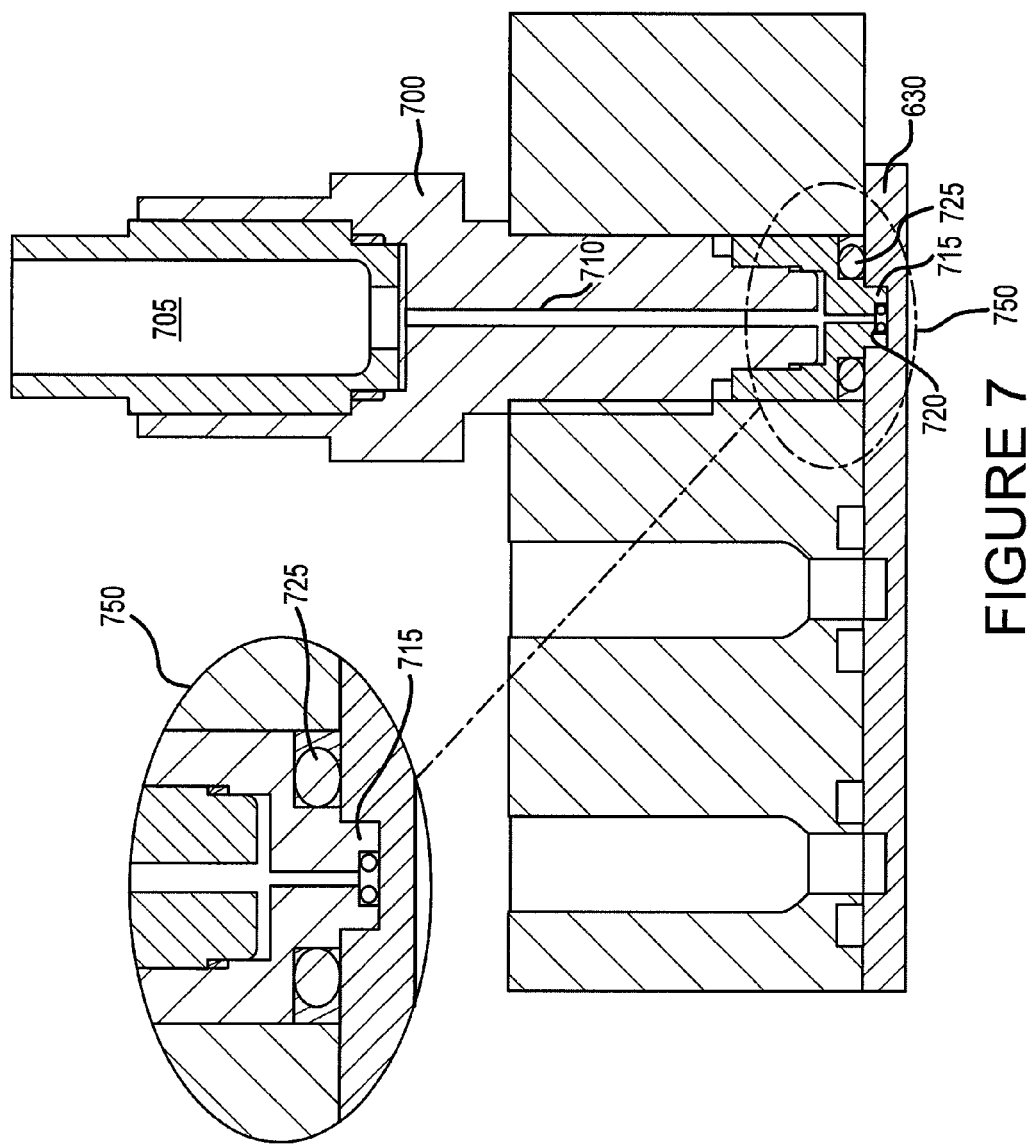
FIG. 7 is a schematic illustration of a cross-section of a sample loading ferrule 700 that may be used in some embodiments of the present invention.

Any of a variety of suitable plumbing ferrules may be used to implement the ferrules 622 and 624. In some examples, a fluid chamber may be provided within a plumbing ferrule, and a low-dead-volume interconnection provided to the microfluidic chip 630. FIG. 7 is a schematic illustration of a cross-section of a sample loading ferrule 700 that may be used in some embodiments of the present invention. A fluid chamber 705 is provided within the ferrule 700 and is in fluid communication with a microfluidic chip 630 through a narrower channel 710. The ferrule 700 has a lower portion 715 configured for insertion into a via defined by the microfluidic chip 630. The via may be in fluidic communication with a microfluidic channel or chamber on the microfluidic chip 630. An O-ring 720 is provided at the end of the portion 715, and is configured to form a portion of the microfluidic channel or chamber on the microfluidic chip 630. In particular, the O-ring 720 may be implemented using a material having sufficient hardness it may not sag or dip into the microfluidic channel or chamber on the microfluidic chip 630 and may form a portion of an upper surface of that microfluidic channel or chamber. A second O-ring 725 may be provided to seal a wider portion of the ferrule 700 to a surface of the microfluidic chip 630. An exploded view of region 750 is also shown in FIG. 7. The O-ring 725 is provided between a wide portion of the ferrule 700 and an upper surface of the microfluidic chip 630. A narrower portion of the ferrule 700 having O-ring 715 at its end, is inserted into a via in the microfluidic chip 630.

Filters or valves may be provided in the ferrule 700, such as between the chamber 705 and the channel 710 to retain fluid in the chamber 705 when desired for a sample preparation process. In one example, an immunodepletion resin may be provided in the chamber 705. As sample fluid passes through the immunodepletion resin, proteins may be retained by the resin. Sample fluid introduced to the microfluidic device 630 may then be free of, or have a reduced concentration of, the protein(s) captured by the immunodepletion resin. Other sample preparation steps may be performed in the chamber 705 instead of or in addition to immunodepletion.

The microfluidic chip 630, fluid distribution manifold 605, electrical interconnect board 610, and fluid distribution manifold 620 may be secured together using substantially any suitable interconnection mechanism. In some examples, screws or other fasteners may be used to compress the various components towards one another.

Figure 8:
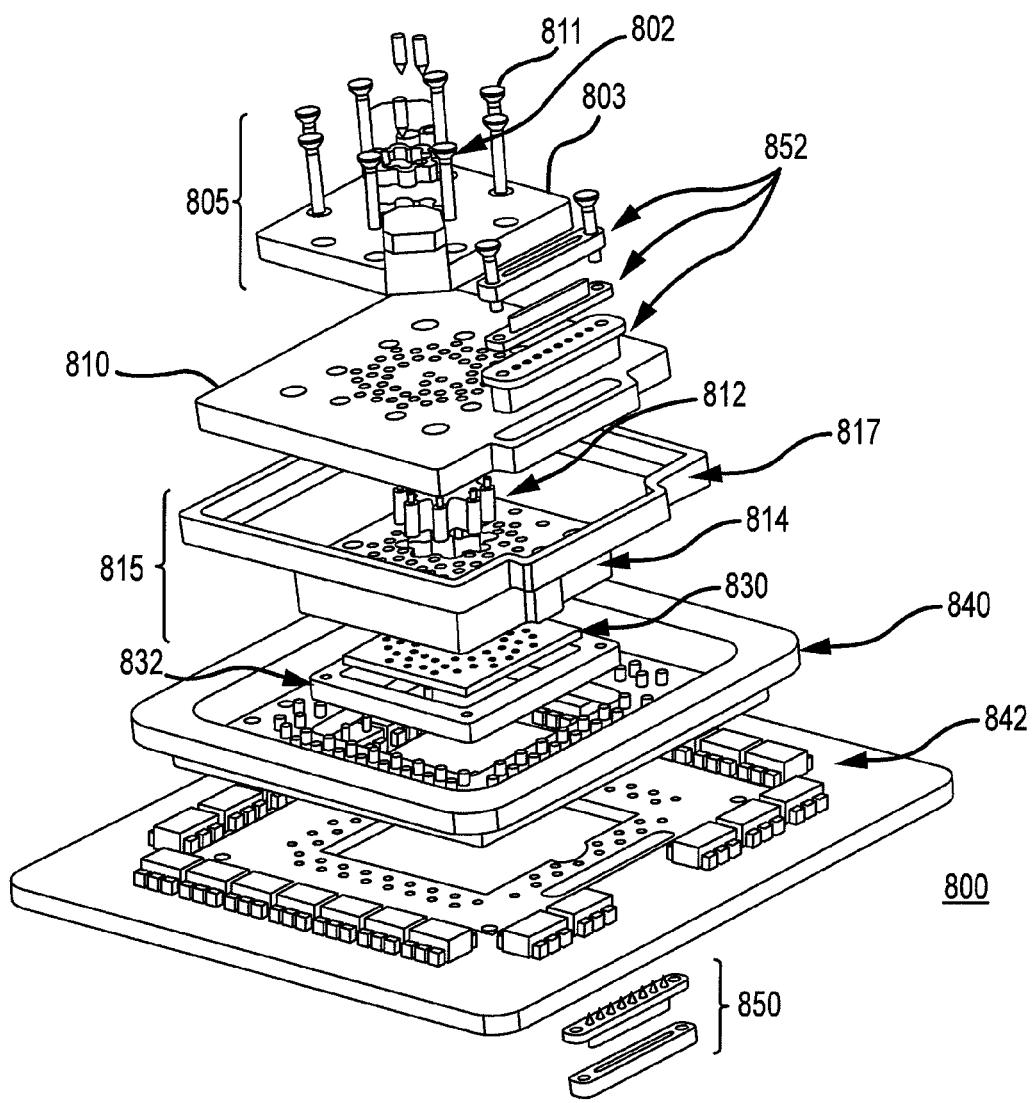
FIG. 8 is a schematic illustration of an exploded view of a microfluidic system 800 according to an embodiment of the present invention.

FIG. 8 is a schematic illustration of an exploded view of a microfluidic system 800 according to an embodiment of the present invention. The microfluidic system 800 includes a fluid distribution manifold 805, which may include an insert member 802 and a manifold base 803. The microfluidic system 800 also includes an electrical interconnect board 810 and another fluid distribution manifold 815, which may include an insert member 812 and a fluid manifold base 814. The electrical interconnect board 810 may be enclosed by a frame 817. A microfluidic chip 830 may be secured to the fluid distribution manifold 815 with another frame 832. As generally described above, the fluid distribution manifolds 805, 815, electrical interconnect board 810, and/or microfluidic chip 830 may form a cartridge. Screws, such as the screw 811, may be used to fasten components of the cartridge together. The cartridge may be received by a cartridge carrier 840 mounted on an electrical multiplex board 842. Fluid connectors 850 and 852 may be provided on the components to route fluids from an external source to the fluid distribution manifold 805 and/or fluid distribution manifold 815 for routing to the microfluidic chip 830.

Fluid distribution manifolds such as the fluid distribution manifolds 805 and 815 have generally been described above and many include an insert member and a manifold base forming at least one substantially closed channel within the fluid distribution manifold for fluid routing. In the microfluidic system 800, fluid from an external source may be coupled to one or more fluid connectors 850 which may be in fluid communication with the fluid connectors 852 of the cartridge. Fluids may be routed from one or more fluid connectors 852 to the insert member 802 using tubing or other fluid connection mechanism. Fluid may then be routed by the fluid distribution manifold 805 to another fluid distribution manifold 815 for further routing, and fluid connection to multiple locations on the microfluidic chip 830.

As has been described above, the electrical interconnect board 810 may include one or more through-holes with conductive sidewalls. A through-hole may define at least a portion of a fluid reservoir along with the fluid distribution manifold 815 or 805. The electrical interconnect board 810 may include conductive traces connecting the conductive sidewalls to externally-accessible electrodes. The externally-accessible electrodes, as will be described further below, may make an electrical connection to the electrical multiplex board 842 through the carrier 840. The through-holes of the electrical interconnect board 810 may be sized to receive one or more of the protrusions on the fluid manifold base 814 and/or fluid insert member 812. Recall the protrusions shown in greater detail on fluid manifold base 300 and insert member 100 of FIG. 4. Similar protrusions may be provided on the fluid manifold base 814 and/or insert member 812 of FIG. 8. The protrusions may be press-fit into the through-holes of the electrical interconnect board 810, forming a fluid-tight seal between the electrical interconnect board 810 and the fluid manifold base 814 and/or insert member 812. In this manner, multiple fluid paths may exist between individual ones of the through-holes of the electrical interconnect board 810 and the through-holes of the fluid manifold base 814 and/or fluid insert member 812. The fluid paths may then extend to individual input ports of the microfluidic chip 830. Fluid introduced to or retained in the fluid paths may be energized using electrodes on the electrical interconnect board 810 which are exposed to the fluid in the through-holes of the electrical interconnect board. Accordingly, by pressing the fluid manifold base and fluid insert member into the electrical interconnect board, electrical and fluidic connections may be established to fluid paths in fluid communication with the microfluidic chip.

In this manner, fluid and electrical interconnections may be made by placing a cartridge including a fluid distribution manifold, electrical interconnect board, and/or microfluidic chip onto a carrier and electrical multiplex board, as will now be described further below. Components of the cartridge may be held together by screws or other fasteners and may be secured by a frame, such as the frame 817 in FIG. 8. Any suitable machinable material may be used to implement the frame 817, and in some embodiments, all or portions of the frame 817 may be implemented using a magnetized material for magnetic connection to the carrier 840, as will be described further below.

Figure 9:
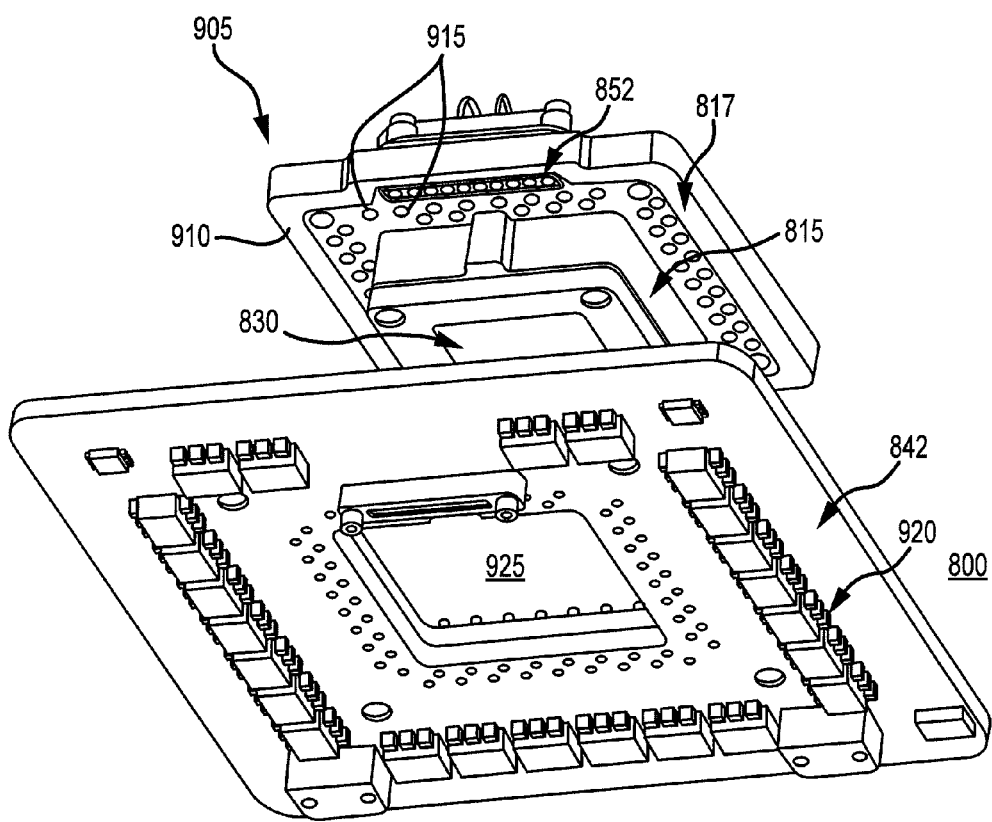
FIG. 9 is a schematic illustration of a bottom-up view of the microfluidic system 800.

Having described components of a microfluidic system above, mechanisms for making fluid and electrical interconnects between a cartridge and an electrical multiplex board will now be described. FIG. 9 is a schematic illustration of a bottom-up view of the microfluidic system 800 showing a cartridge 905 and electrical multiplex board 842 having a carrier (not seen in FIG. 9). The cartridge 905 includes the fluid distribution manifold 805 (not seen in FIG. 9), the fluid connectors 852, the electrical interconnect board 810, the frame 817, the fluid distribution manifold 815, and the microfluidic chip 830. A surface 910 of the electrical interconnect board 810 facing the electrical multiplex board is provided with externally-accessible electrodes 915. Individual ones of the externally-accessible electrodes 915 may be electrically connected to one or more through-holes having conductive sidewalls, as generally described above. That is, a voltage or current may be applied to a fluid reservoir by applying a voltage or current to one or more of the externally-accessible electrodes 915. In the embodiment shown in FIG. 9, the externally-accessible electrodes 915 may be implemented as recessed conductive electrodes.

The voltage multiplex board 842 may include one or more voltage relays 920. The voltage relays 920 operate in accordance with control signals to connect one or more voltage sources to one or more electrodes disposed on the carrier (not seen in FIG. 9) receiving the cartridge, as will be described further below. The multiplex board 842 and carrier define an opening 925 into which the microfluidic chip 830 and a portion of the fluid distribution manifold 815 will extend once the cartridge 905 is seated on the electrical multiplex board 842 and carrier. In this manner a surface of the microfluidic chip 830 may remain visible to users or detectors viewing the chip 830. A frame securing the microfluidic chip 830 to the fluid manifold base 814 may secure the microfluidic chip 830 around one or more edges of the microfluidic chip 830, leaving a relatively large area of the microfluidic chip accessible to detectors or users viewing the chip 830. The opening 925 and frame 832 accordingly allow for a relatively large viewing area for observing the microfluidic chip. Electrical and fluidic connections may not obscure the viewing area in some embodiments due in part to their positioning as shown.

Figure 10:
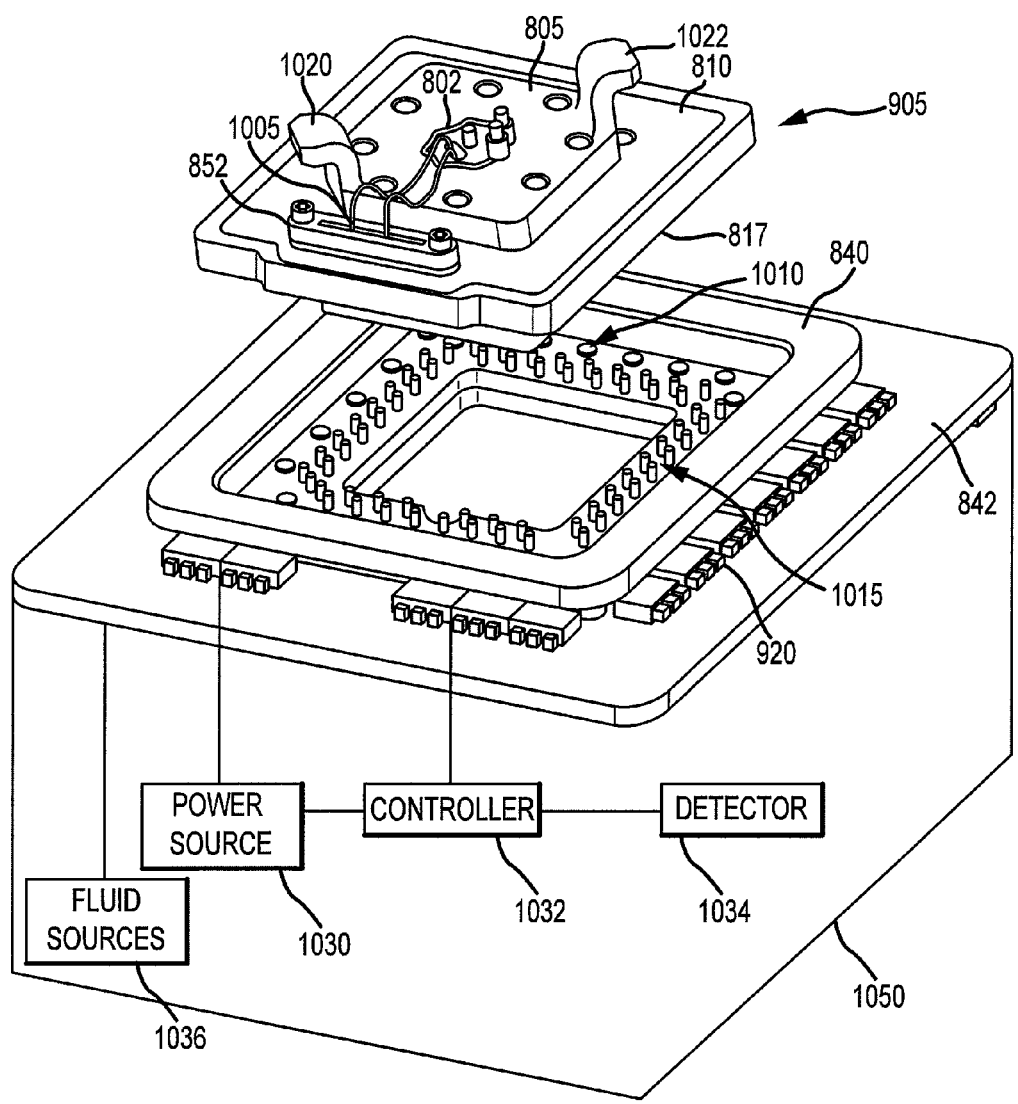
FIG. 10 is a schematic illustration of a top-down view of the microfluidic system 800.

FIG. 10 is a schematic illustration of a top-down view of the microfluidic system 800 showing the cartridge 905 and electrical multiplex board 842 and carrier 840. The cartridge 905 includes the fluid distribution manifold 805, the fluid connectors 852, the electrical interconnect board 810, the frame 817, the fluid distribution manifold 815 (not seen in FIG. 10), and the microfluidic chip 830 (not seen in FIG. 10). Tubing 1005 can be seen in FIG. 10 connecting individual ones of the fluid connectors 852 to input ports of the insert member 802. A surface of the carrier 840 facing the cartridge 905 may be seen in FIG. 10. The surface includes magnets 1010 and pins 1015. The pins 1015 are arranged for interconnection with the externally-accessible electrodes 915 on a surface of the electrical interconnect board 810. Accordingly, when the cartridge 905 is placed on the carrier 840, electrical connection is achieved between individual ones of the pins 1015 and corresponding externally-accessible electrodes 915 of the electrical interconnect board 810. It may be appreciated that a large number of electrical interconnects may be simultaneously made in this manner. The number of electrical interconnects may vary and may be more than 10, more than 20, more than 30, more than 40, more than 50, more than 60, more than 70, or more than 80, in some embodiments. Other numbers of interconnects may be used. In the embodiment shown in FIG. 10, 71 electrical interconnects may be simultaneously made between the cartridge 905 and the voltage multiplex board 842 when the cartridge 905 is place on the carrier 840.

Although the externally-accessible electrodes 915 are shown as recessed in FIG. 9 and the pins 1015 of FIG. 10 arranged to insert into a well forming the recessed externally-accessible electrodes 915, other configurations may be used. In some embodiments, the carrier 840 may provide recessed electrodes while protruding pins may be provided on the electrical interconnect board, for example. In other embodiments, the electrodes on both the electrical interconnect board and the carrier may be planar.

To secure the cartridge 905, to the carrier 840, simple gravitational force may be relied on in some embodiments. In some embodiments, magnetic connection may be made between the cartridge 905 and the carrier 840. For example, all or a portion of the frame may be made from a magnetic material, and one or more magnets 1010 may be provided on the carrier 840. In this manner, the cartridge 905 may be secured to the carrier 840 by magnetic force. Although the frame 817 is shown as supplying the magnetic material of the carrier 905, in other examples a magnetic material may be provided on the electrical interconnect board or other location on the cartridge 905. The magnets 1010 are arranged to correspond to locations of the magnetic material on the cartridge 905. In the embodiment of FIG. 10, the magnets 1010 correspond to a shape of the magnetic frame 817. Any number of magnets may be used. As shown in FIG. 10, the cartridge 905 may include handles 1020, 1022, or other protrusion that may facilitate gripping the cartridge 905 for placement onto the carrier 840. The cartridge 905 may be held and placed onto the carrier 840 by a human user or a machine.

The electrical multiplex board 842 may in some embodiments be coupled to one or more of a power source 1030, controller 1032, fluid source(s) 1036, and/or detector 1034. The power source 1030, controller 1032, fluid source(s) 1036 and/or detector 1034 may also be in communication with one another and may be housed in a housing 1036 in some embodiments, with a surface of the housing formed in part by the electrical multiplex board 842. The power source 1030 may be a voltage or a current source, for example, and may be in electrical communication with one or more of the voltage relays 920. The controller 1032 may provide control signals to one or more of the voltage relays 920 to couple power from the power source 1030 to selected ones of the pins 1015 for applying a voltage or current to fluid reservoirs. In this manner, for example, fluids may be electrophoretically moved through the microfluidic chip 830. The controller 1032 may include one or more processing unit(s) and may be in communication with a memory encoded with instructions causing a predetermined set of control signals to be generated that may implement a particular microfluidic analysis within the microfluidic chip 830. In this manner, automated microfluidic analysis may be performed that may not require a skilled technician for operation. The fluid source(s) 1036 may be in fluid communication with the connectors 850 on the electrical multiplex board. Any type of fluids may be used, including, for example, biological fluid samples containing target analytes of interest, including, but not limited to, proteins, DNA, RNA, or explosive residue. Other types of fluids that may be used include, but are not limited to, buffer fluids and wash fluids. The detector 1034 may be positioned to receive a signal from the microfluidic chip 830. The signal may be an optical, electrical, or other type of signal, and the detector 1034 may accordingly be configured to receive an optical, electrical, or other signal. The controller 1032 may also generate control signals for the detector 1034 to control when or for how long the detector 1034 collects a signal from the microfluidic chip 830. In some examples, the detector 1034 may be an optical detector configured to detect a label affixed to a target analyte of interest in a sample loaded into the microfluidic chip 830. The detector 1034 may communicate or store data regarding the signals received from the microfluidic ship 830. The data may be stored in a memory in electronic communication with the detector 1034 and/or communicated through any interface, wired or wireless.

Fluid distribution manifolds, cartridges, and microfluidic systems have been described above. Embodiments of the present invention may advantageously provide fluid routing, and may provide for the making of electric and fluidic interconnects between an electrical multiplex board and a cartridge having a microfluidic chip. Some methods of using these devices will now be described further below. It should be noted that embodiments of the present invention provide for fluid routing, fluid interconnection, and/or electrical interconnection to a microfluidic chip. The fluidic and/or electrical connections may be used to perform substantially any microfluidic analysis techniques and carry substantially any fluid(s). Accordingly, examples of methods described herein are related to methods for using the interconnections described, and a variety of microfluidic analysis techniques may be performed using the resulting system.

Figure 11:
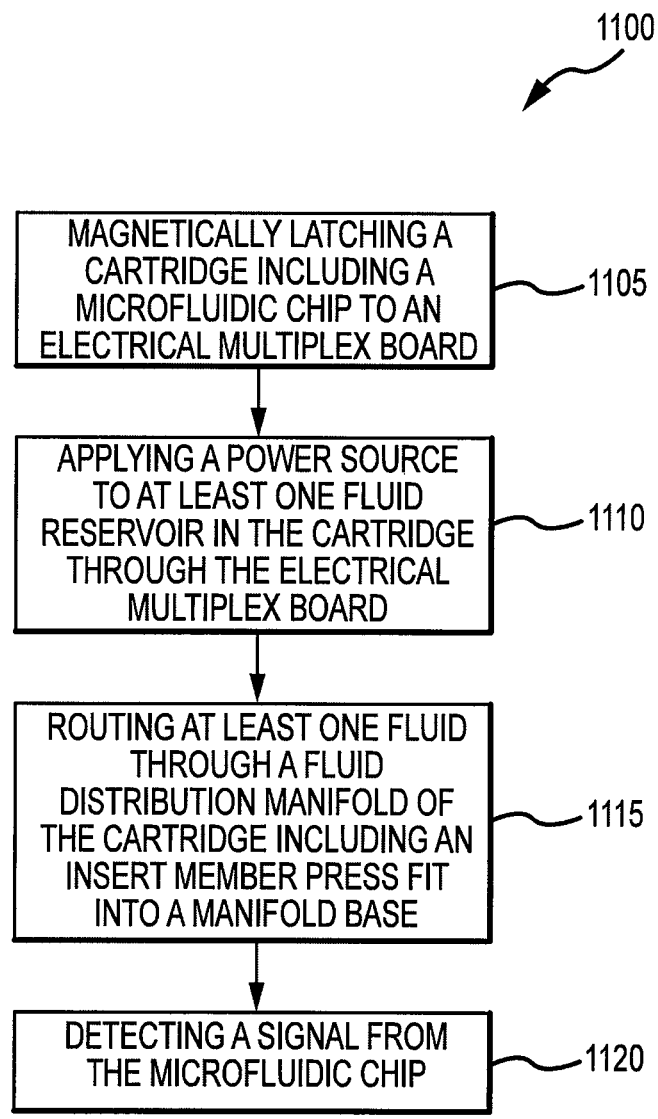
FIG. 11 is a schematic illustration of a method 1100 in accordance with an embodiment of the present invention.

FIG. 11 is a schematic illustration of a method 1100 in accordance with an embodiment of the present invention. In block 1105, a cartridge including a microfluidic chip may be magnetically latched to an electrical multiplex board. In some embodiments, magnetic latching may not occur, and the cartridge may be placed onto or into an electrical multiplex board. Referring back to FIG. 10, recall that the cartridge 905 may magnetically latch to the electrical multiplex board 842 through the magnetic frame 817 and magnets 1010. Magnetically latching the cartridge to the electrical multiplex board, or otherwise placing the cartridge into or onto the electrical multiplex board may form a plurality of fluid and/or electrical connections. For example, referring back to FIG. 10, placing the cartridge 905 onto the electrical multiplex board 842 having the carrier 840 creates electrical connections between the pins 1015 and the externally-accessible electrodes of the electrical interconnect board 810. Further, fluidic connections are made between the fluid connectors 852 and the fluid sources 1036.

Referring again to FIG. 11, in block 1110 a power source may be applied to at least one fluid reservoir in the cartridge through the electrical multiplex board. The power source may include a voltage or a current source. For example, referring back to FIG. 10, the power source 1030 may be coupled to one or more voltage relays 920. Responsive to a control signal from the controller 1032, individual voltage relays 920 may couple the power source 1030 to selected ones of the externally-accessible electrodes on the electrical interconnect board 810. The externally-accessible electrodes on the electrical interconnect board 810 are in electronic communication with conductive sidewalls of through-holes forming a portion of a fluid reservoir. In this manner, the power source 1030 may be coupled to the fluid reservoir.

Referring again to FIG. 11, in block 1115 at least one fluid may be routed through a fluid distribution manifold of a cartridge including an insert member press-fit into a manifold base. The fluid may be routed using pressure-driven flow, or substantially any other flow mechanism, including electrophoretic flow. Referring back to FIG. 10, Fluid from one or more of the fluid sources 1036 may be routed through the manifold 805 including insert 802 and/or manifold 815 (not shown in FIG. 10).

Fluids are routed through a fluid distribution manifold, and may then enter a microfluidic chip for analysis. They may be drawn through the microfluidic chip in accordance with control signals generated by a controller and applied to the fluid reservoirs. For example, electrophoretic flow may be initiated, and/or stopped, by the application or removal of voltages from particular fluid reservoirs within a fluid routing manifold.

Referring again to FIG. 11, in block 1120 a signal may be detected from the microfluidic chip. For example, the detector 1034 of FIG. 10 may detect a signal from the microfluidic chip. As described above, substantially any signal may be detected, and the presence and/or absence of a target analyte in a sample may correspond to the received signal in some embodiments. Accordingly, embodiments of methods according to the present invention may detect a target analyte in a sample through use of fluidic and/or electronic interconnections described above. Signals detected may be stored and/or transmitted for use or analysis by users or other computer systems.

The blocks 1105, 1110, 1115, and 1120 may occur in other orders in other embodiments, and some blocks may not be used in some embodiments. Once a microfluidic analysis has been performed using one cartridge with a microfluidic chip, the cartridge may be removed by removing it from the electrical multiplex board. In this manner, one or more electrical and/or fluidic connections to the cartridge may be broken. Another cartridge may be magnetically latched or otherwise placed on the electrical multiplex board, and the blocks of FIG. 11 may be repeated. In this manner, microfluidic analysis may occur on multiple microfluidic chips by placing them in turn onto the electrical multiplex board.

From the foregoing it will be appreciated that, although specific embodiments of the invention have been described herein for purposes of illustration, various modifications may be made without deviating from the spirit and scope of the invention.

What is claimed is:

1. A fluid distribution manifold comprising:
   an insert member comprising a first surface, a second surface opposite the first surface, and a sidewall extending between the first surface and the second surface, wherein the insert member at least partially defines at least one channel on the first surface, wherein the at least one channel is configured for fluid communication between an inlet location and a plurality of outlet locations provided on the first surface, and wherein the at least one channel is open along a length of the at least one channel between the inlet location and at least one of the plurality of outlet locations;
   a manifold base comprising a first surface and a second surface opposite the first surface, wherein the manifold base at least partially defines an indentation in the first surface, the indentation comprising a recessed surface and a sidewall, the indentation having a shape configured to receive the insert member such that the insert member fills the indentation and the insert member is attached to the manifold base by friction between respective sidewalls of the insert member and the indentation; and
   wherein at least one of the manifold base and the insert member at least partially defines a fluid inlet in fluid communication with the inlet location, and wherein at least one of the manifold base and the insert member at least partially defines a plurality of fluid outlets, wherein ones of the fluid outlets are in fluid communication with respective ones of the plurality of outlet locations.

2. The fluid distribution manifold of claim 1, wherein a first portion of the recessed surface forms a wall of the at least one channel when a second portion of the recessed surface of the indentation adjacent to the first portion is in contact with the first surface of the insert member to form a substantially closed channel that provides a fluid-tight seal between the insert member and the manifold base.

3. The fluid distribution manifold of claim 1, wherein the insert member at least partially defines the fluid inlet from the second surface of the insert member to the inlet location.

4. The fluid distribution manifold of claim 1, wherein the manifold base at least partially defines the fluid inlet from the second surface of the manifold base to the inlet location.

5. The fluid distribution manifold of claim 1, wherein the insert member at least partially defines at least one of the fluid outlets from the second surface of the insert member to at least one of the outlet locations.

6. The fluid distribution manifold of claim 1, wherein the manifold base at least partially defines at least one of the fluid outlets from the second surface of the manifold base to at least one of the outlet locations.

7. The fluid distribution manifold of claim 1, wherein a size of the insert member is slightly larger than a size of the indentation of the manifold base, wherein the indentation is configured to deform to accommodate the insert member by press-fitting.

8. The fluid distribution manifold of claim 1, wherein the fluid inlet is configured to receive a fluid from an external source.

9. The fluid distribution manifold of claim 1, wherein individual of the plurality of outlets are configured to provide a fluid from the inlet to respective locations of a microfluidic chip.

10. The fluid distribution manifold of claim 1, wherein the at least one channel has a width of less than 500 microns.

11. The fluid distribution manifold of claim 1, wherein the at least one channel has a width of less than 200 microns.

12. The fluid distribution manifold of claim 1, wherein the fluid communication comprises a route from the inlet location to the plurality of outlet locations.

13. The fluid distribution manifold of claim 1, wherein the fluid inlet and fluid outlets extend from the first surface of the insert member to the second surface of the insert member.

14. The fluid distribution manifold of claim 1, wherein the fluid inlet and fluid outlets extend from the second surface of the insert member to the second surface of the manifold base.

15. The fluid distribution manifold of claim 1, wherein the insert member further comprising a raised portion on the first surface and wherein the channel is defined in the raised portion, and wherein the indentation is a primary indentation, the manifold base further comprising a secondary indentation in the primary indentation, the secondary indentation configured for insertion of the raised portion therein.

* * * * *